United States Patent [19]

Hutchins et al.

[11] Patent Number: 5,246,860
[45] Date of Patent: Sep. 21, 1993

[54] TRACER CHEMICALS FOR USE IN MONITORING SUBTERRANEAN FLUIDS

[75] Inventors: Richard D. Hutchins, Placentia; Dennis L. Saunders, Anaheim, both of Calif.

[73] Assignee: Union Oil Company of California, Los Angeles, Calif.

[21] Appl. No.: 829,118

[22] Filed: Jan. 31, 1992

[51] Int. Cl.$^5$ .................... G01N 33/24; G01N 33/28
[52] U.S. Cl. ................................ 436/27; 116/250; 116/252; 436/29; 436/56
[58] Field of Search ................. 436/27, 56, 28, 29; 116/250, 252

[56] References Cited

U.S. PATENT DOCUMENTS 3,508,876  4/1970  Polly .
4,330,153  5/1982  Di Giacomo et al. ............ 299/4 X
4,555,489  11/1985  Schmitt ................................ 436/27

OTHER PUBLICATIONS

Adams et al., "*Tracer Developments: Results of Experimental Studies*", Standard Geothermal Program, (Jan. 1986).
Adams et al., "*Derivatized Hydrocarbons as Geothermal Tracers*", Geothermal Resources, (1986) pp. 415–420.
Breitenbach et al., "Evaluation of Chemical Tracers for Geothermal Use", Pacific Geothermal Conference, (1982), pp. 229–233.
Chrysikopoulos et al., "*Thermal Stability of Chelated Indium Activable Tracers*", Stanford Geothermal Program (Jan., 1986).
Adams, M. C., "*Tracer Stability and Chemical Changes in an Injected Geothermal fluid During Injection–Backflow Testing at the East Mesa Geothermal Field,*" Standard Geothermal (Jan. 22, 1985).
Bowman, R. S., "*Evaluation of Some New Tracers for Soil Water Studies*", Soil Science Soc. of America Journal, vol. 48, No. 5 (Sep.–Oct. 1984), pp. 987–993.
Bowman et al., "*An Expanded Suite of Fluorobenzoate Tracers for Soil and Ground Water Investigators*", Submitted to Ground Water in Sep. 1990.
Smart et al., "*An Evaluation of Some Fluorescent Dyes for Water Tracing*", Water Resources Research, vol. 13, No. 1 (Feb. 1977), pp. 15–33.
SPE 15092, Heisler, "*Interpretation of Radioactive Tracer Results in a Steamdrive Project,*" (1986).
SPE 8270, Tester, et al., "*Interwell Tracer Analysis of a Hydraulically Fractured Granite Geothermal Reservoir.*"
McCabe et al., "*Radioactive Tracers in Geothermal Underground Water Flow Studies*", Geothermics, vol. 12, No. 2/3, pp. 83–110 (1983).
Dennis et al., "*Radioactive Tracers Used to Characterize Geothermal Reservoirs*", Geothermal Resources Council, Transactions vol. 5, (Oct. 1981) pp. 329–332.
Gudmundsson et al., "Doublet Tracer Testing in Klamath Falls, Oregon" Proceedings 9th Workshop, Geothermal Reservoir Engineering, Stanford, Calif., (Dec. 1983), pp. 331–337.
SPE 7960, "*Radioactive Tracer Adsorption Chromatography in Geothermal Reservoirs,*" (1979).
SPE 7867, Handy, et al., "*Thermal Stability of Surfactants for Reservoir Application,*" (1979).
SPE 10777, Al-Khafaja, et al. "*Steam Surfactant Systems at Reservoir Conditions,*" (1982).
SPE 13610, Walkup, Jr., et al. "*Characterization of Tracer Retention Processes and their Effect on Tracer Transport in Fractured Geothermal Reservoirs*" (1985).
Urbino et al., "*Structural Flowpaths of Reinjected Fluids Based on Tracer Tests*", Proc. 8th NZ Geothermal Worshop (1986).

Primary Examiner—Jill A. Johnston
Attorney, Agent, or Firm—Gregory F. Wirzbicki; Shlomo R. Frieman

[57] ABSTRACT

Organic tracers are employed to monitor the movement of subterranean fluids. These organic tracers are (a) stable at elevated temperatures, (b) capable of being detected at low concentrations, and/or (c) not adversely affected by the make-up of at least one subterranean formation. In addition, a plurality of these tracers can be measured by a single analytical technique.

19 Claims, 15 Drawing Sheets

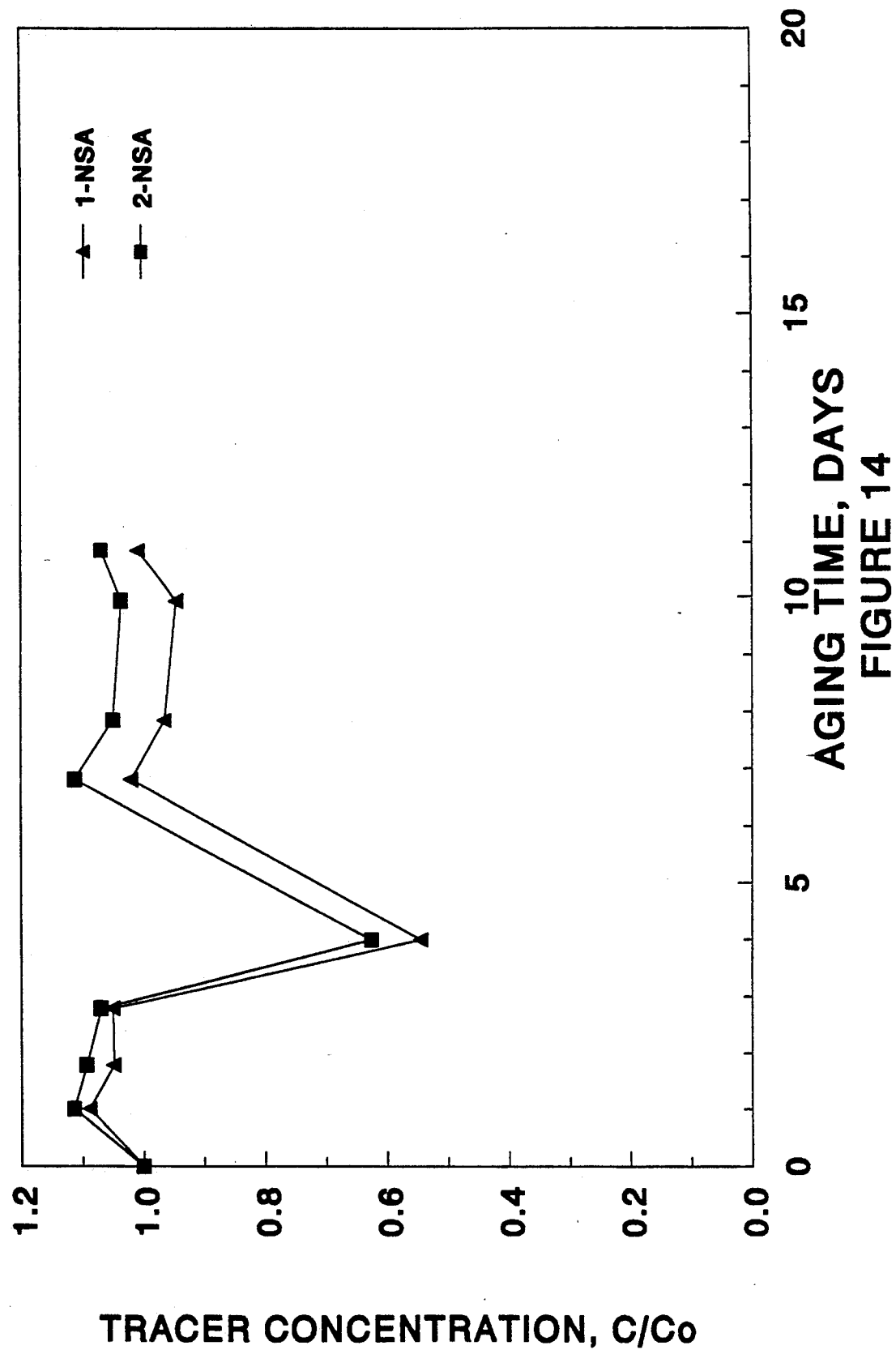

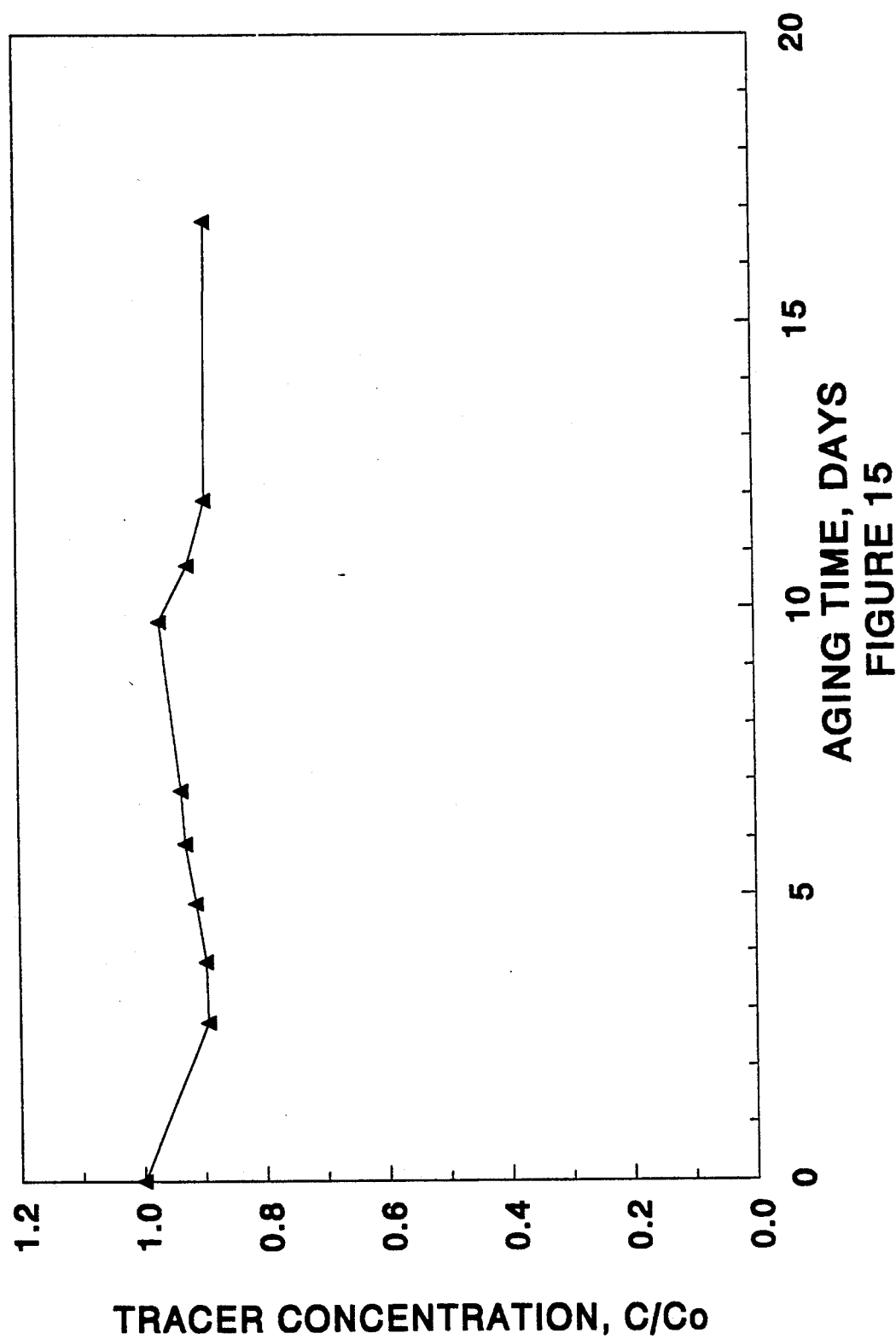

TRACER CHEMICALS FOR USE IN MONITORING SUBTERRANEAN FLUIDS

BACKGROUND

The present invention relates to the use of organic chemicals as tracers for monitoring subterranean fluids. As used in the specification and claims, the term subterranean fluids means aqueous-based fluids (e.g., ground water, geothermal brines, and fluids injected during the course of enhanced oil recovery procedures such as steam floods, carbon dioxide floods, caustic floods, polymer floods, and micellar-polymer floods), and organic-based fluids (e.g., crude oil) produced from a subterranean formation or subterranean reservoir.

In most production reservoirs, the produced brines are injected into the formation for purposes of maintaining reservoir pressure and avoiding subsidence and environmental pollution. In the case of geothermal fields, the brines are also injected to recharge the formation. However, the injected brines can adversely affect the fluids produced from the reservoir. For example, in geothermal fields, the injected brine can lower the temperature of the produced fluids by mixing with the hotter formation fluids. In order to mitigate this problem, the subsurface paths of the injected fluids must be known.

Tracers have been used to label fluids in order to track fluid movement and monitor chemical changes of the injected fluid. Despite their importance to the reservoir operator, very few tracers are presently available. Furthermore, of those that are available, little is known about their stabilities or behavior at the elevated temperatures that typify geothermal resources capable of electric power generation.

Radioactive materials are one class of commonly used tracers. These tracers have several drawbacks. One drawback is that they require special handling because of the danger posed to personnel and the environment. Another drawback is the alteration by the radioactive materials of the natural isotope ratio indigenous to the reservoir—thereby interfering with scientific analysis of the reservoir fluid characteristics. In addition, the half life of radioactive tracers tends to be either too long or too short for practical use.

SUMMARY OF THE INVENTION

In one embodiment, the present invention provides a number of organic compounds suitable for use as tracers in a process for monitoring the flow of subterranean fluids. An exemplary process embodying features of the invention comprises the steps of injecting a tracer-containing fluid into an injection well, producing a subterranean fluid from a production well, and analyzing the produced subterranean fluid for the presence of the tracer. At least one tracer employed in this process is selected from the group consisting of benzene tetracarboxylic acid, methylbenzoic acid, naphthalenesulfonic acid, naphthalenedisulfonic acid, naphthalenetrisulfonic acid, alkyl benzene sulfonic acid, alkyl toluene sulfonic acid, alkyl xylene sulfonic acid, alpha-olefin sulfonic acid, salts of the foregoing acids, naphthalenediol, aniline, substituted aniline, pyridine, substituted pyridine, and mixtures thereof. The alkyl moiety of the alkyl benzene sulfonic acid, alkyl benzene sulfonate, alkyl toluene sulfonic acid, alkyl toluene sulfonate, alkyl xylene sulfonic acid, and alkyl xylene sulfonate contains at least 1 carbon atom, and the olefin moiety contains at least about 3 carbon atoms.

In another process embodying features of the invention, the flow of a plurality of subterranean fluids is monitored. For example, a first fluid is injected into a first injection well and a second fluid is injected into a second injection well. The first fluid contains a tracer different from the tracer present in the second fluid. At least one of the above-described tracers is employed in at least one of the injected fluids. In this version of the invention, any convenient number of injection wells and different tracer-containing fluids are used, and at least one sample from one or more production wells is analyzed to monitor the subterranean fluid movement.

A system for processing a subterranean fluid and a subterranean fluid containing at least one of the above identified tracers are also within the scope of the invention. The system comprises (a) at least one subterranean formation, (b) a production well for producing a subterranean fluid from a first subterranean formation, the production well penetrating at least a portion of the first subterranean formation, (c) an injection well for injecting a tracer-containing fluid into at least a portion of a second subterranean formation, the injection well penetrating at least a portion of the second subterranean formation, and (d) the tracer-containing fluid in at least a portion of the injection well. Typically, the first and second subterranean formations are the same. The previously described tracers are used in this system.

DRAWINGS

The suitability of various chemical compounds tracers for monitoring the flow of subterranean fluids as well as other features, aspects, and advantages of the invention will become better understood with reference to the following description, appended claims, and accompanying drawings where:

Figure 1:
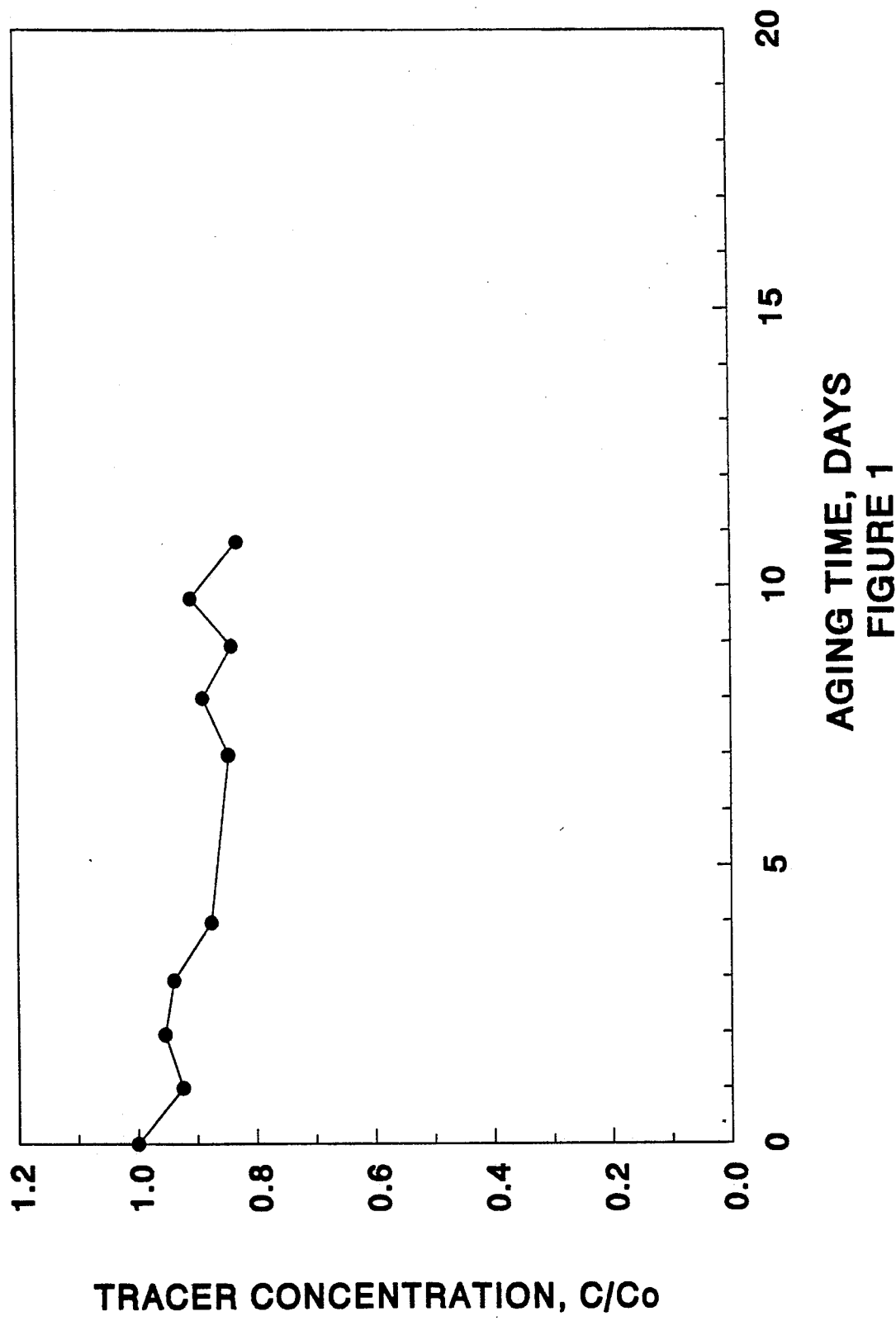
FIG. 1 is a graph depicting the results of a stability test of pyridine at about 260° C. (about 500° F.)
Figure 2:
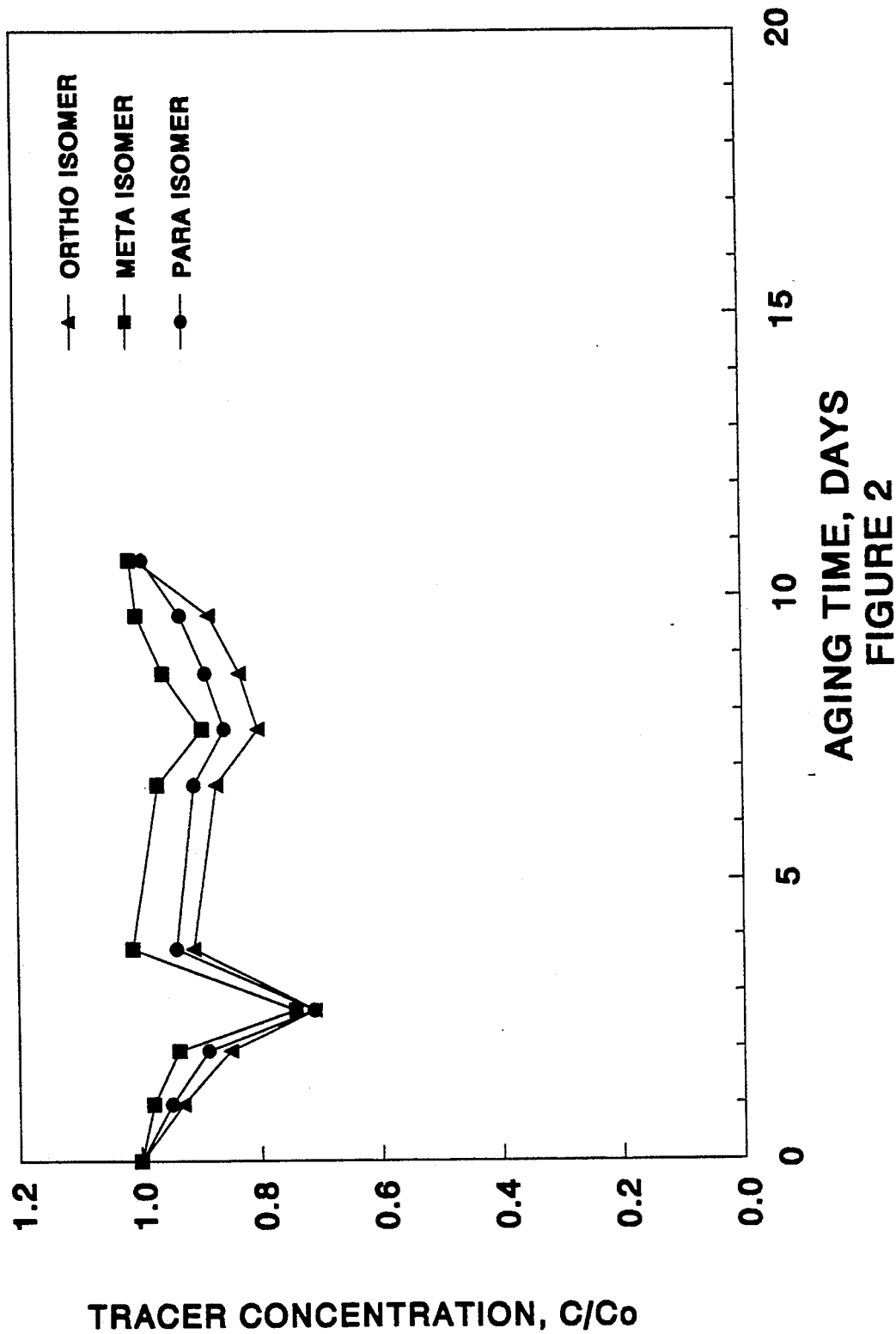
FIG. 2 is a graph depicting the results of stability tests of ortho-, meta-, and para-methylbenzoic acids at about 260° C. (about 500° F.)
Figure 3:
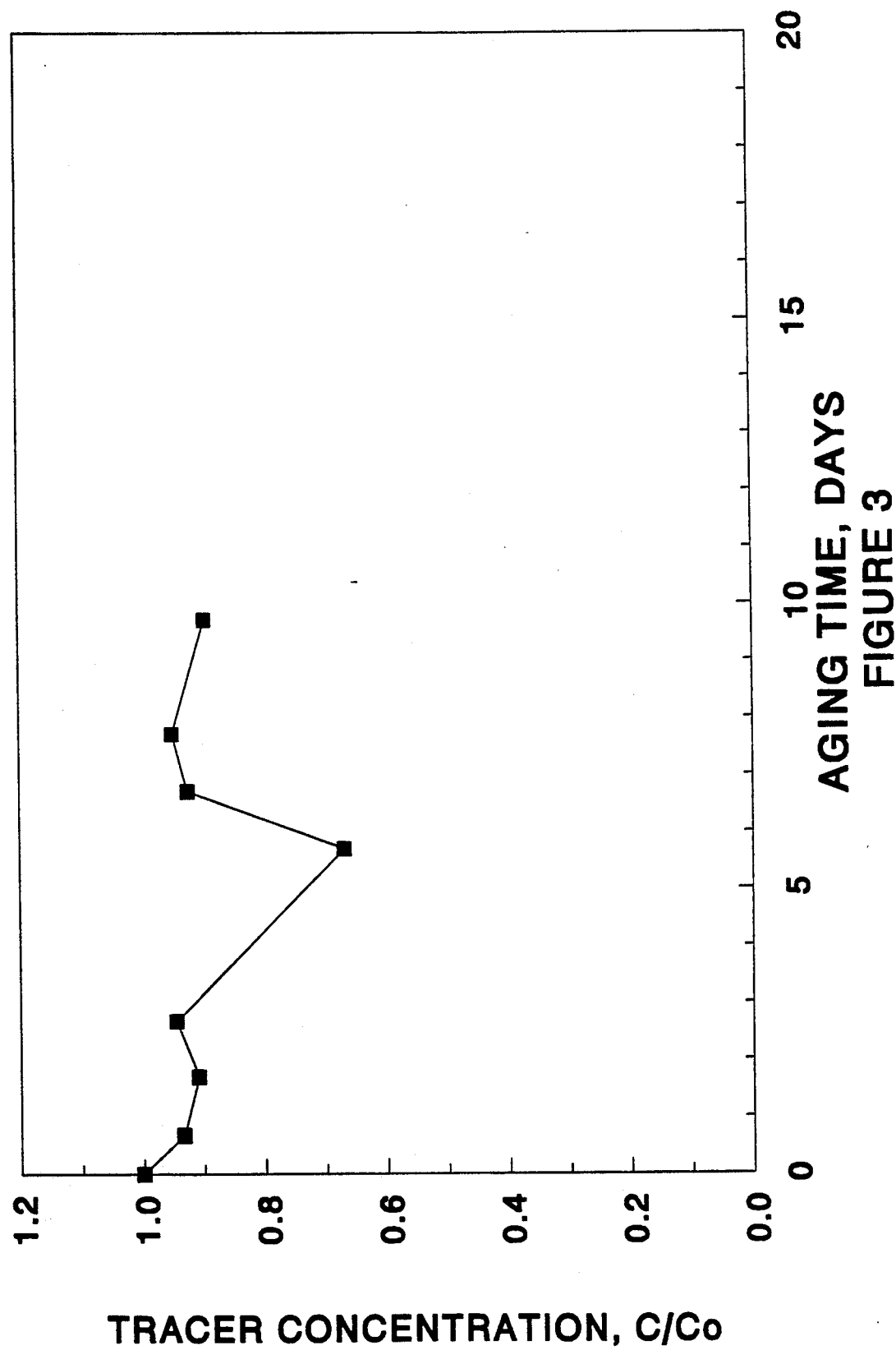
FIG. 3 is a graph depicting the results of a stability test of aniline at about 260° C. (about 500° F.)
Figure 4:
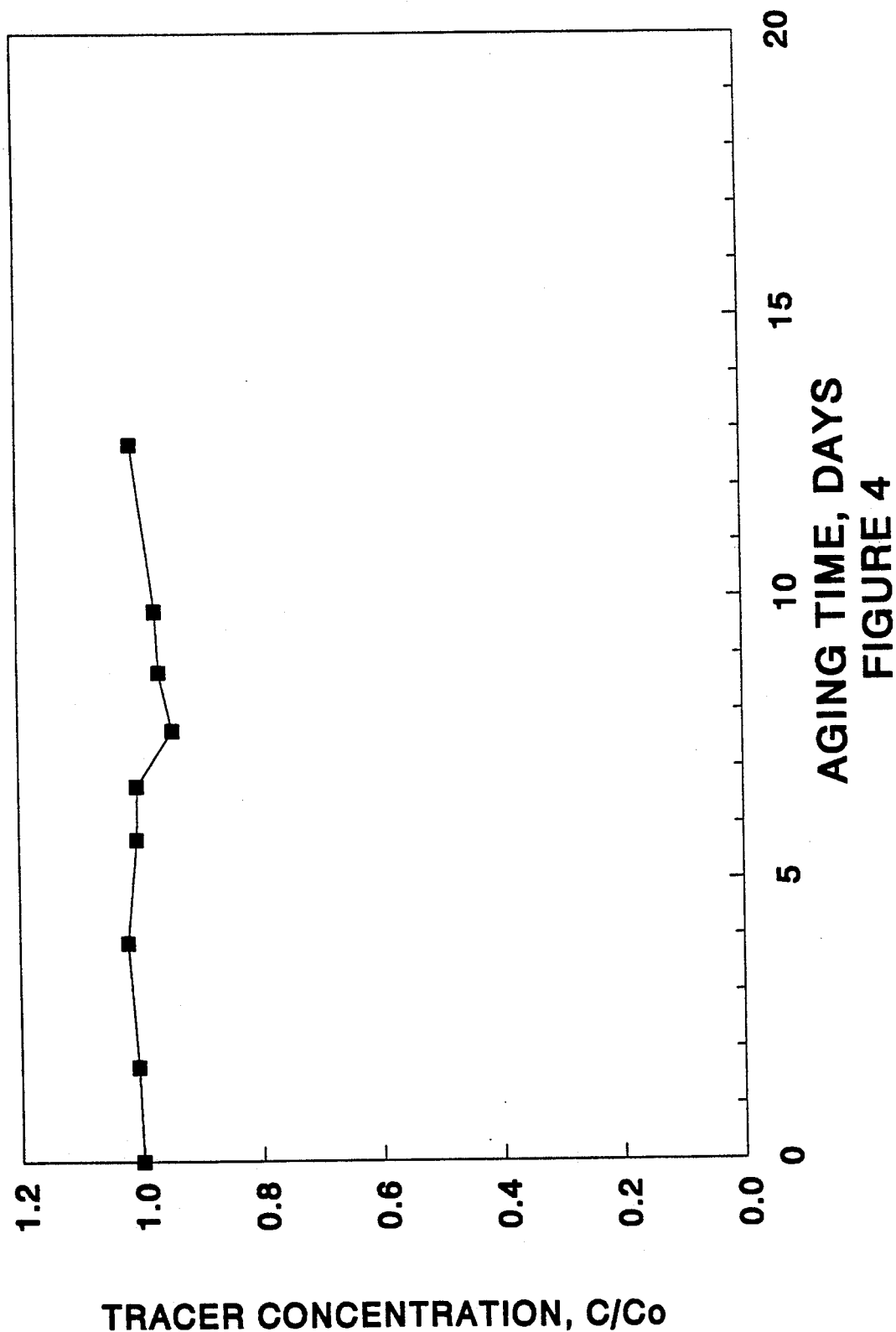
FIG. 4 is a graph depicting the results of a stability test of 1,2,4,5-benzene tetracarboxylic acid at about 260° C. (about 500° F.)
Figure 5:
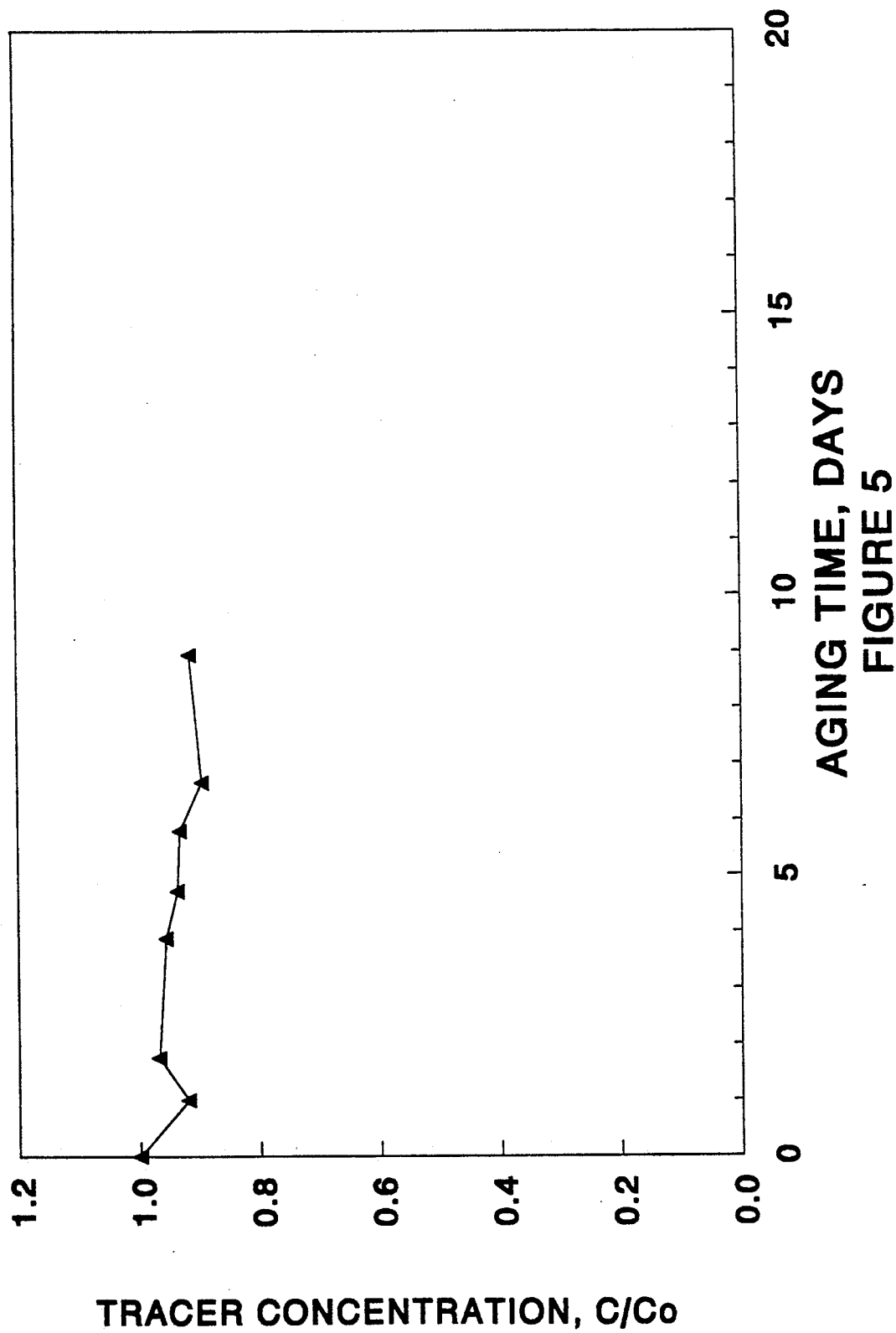
Figure 6:
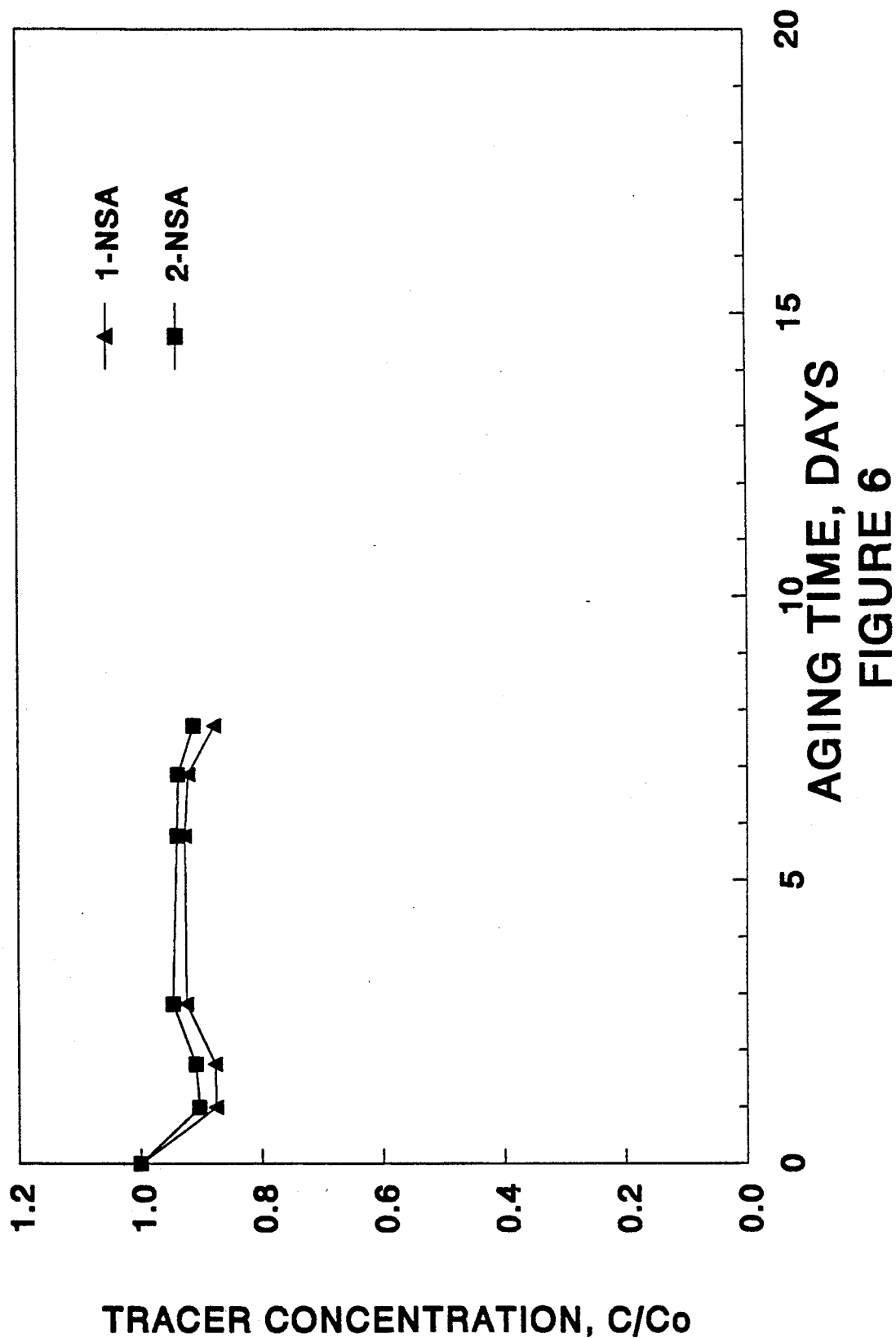
Figure 7:
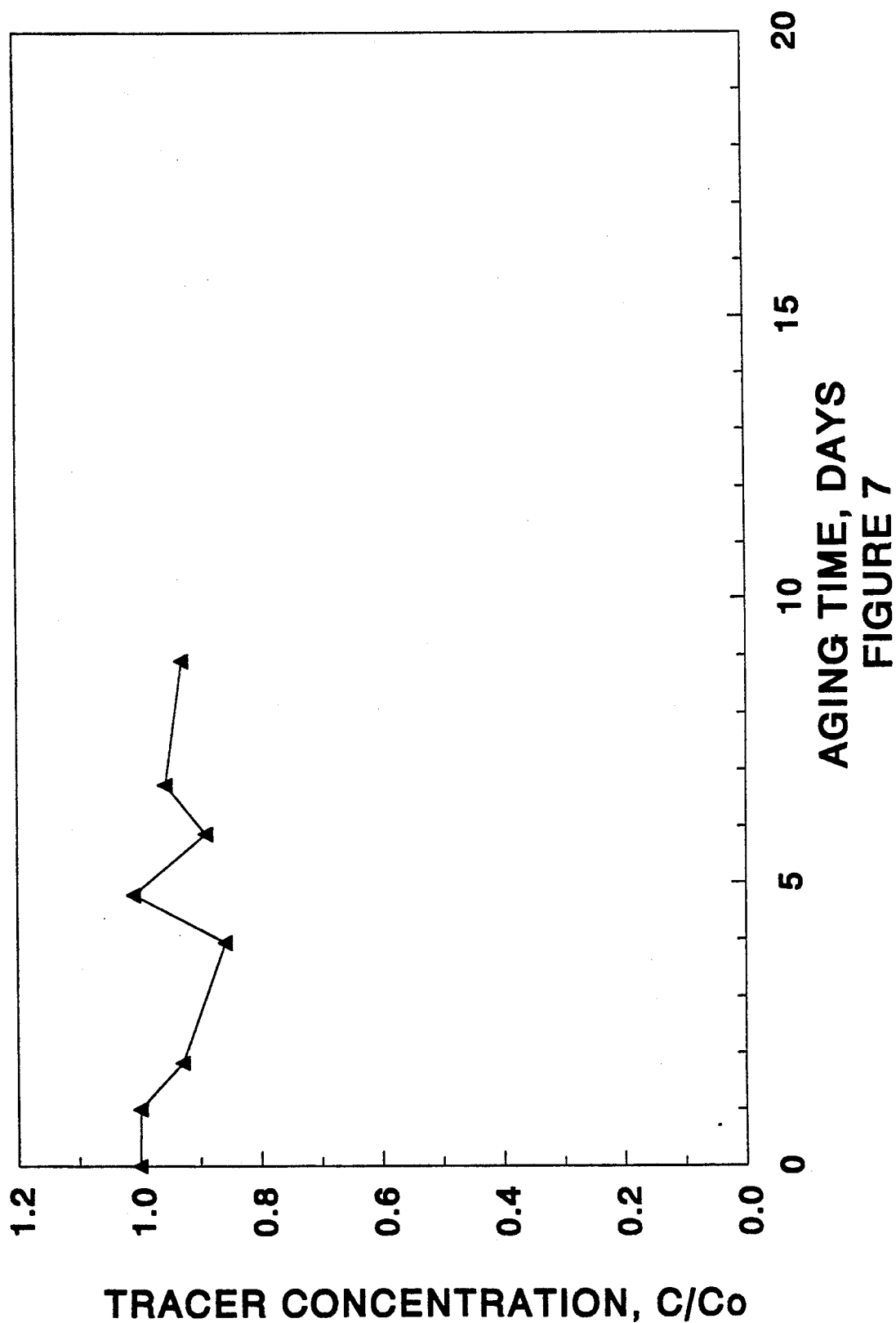
Figure 8:
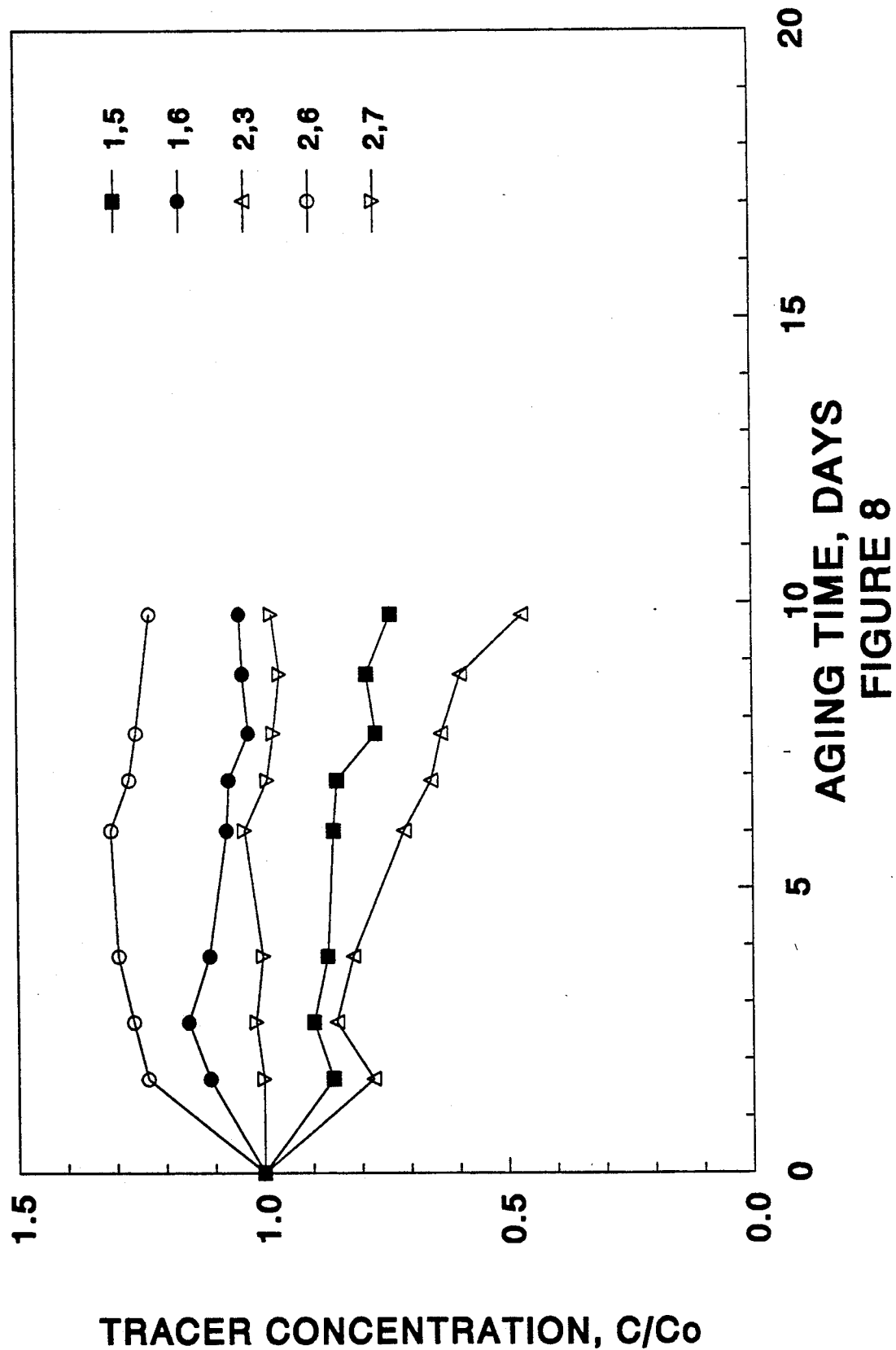
Figure 9:
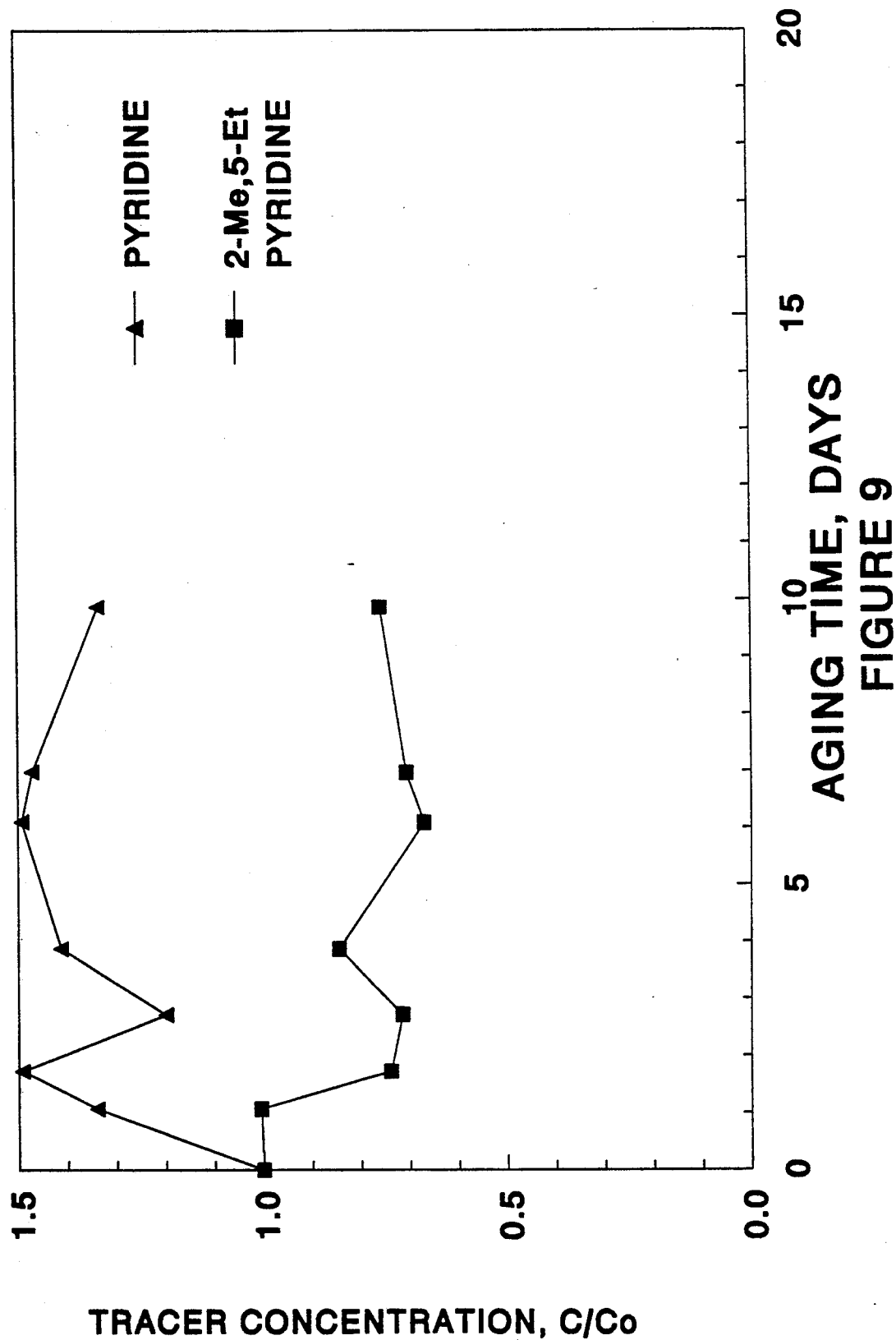
Figure 10:
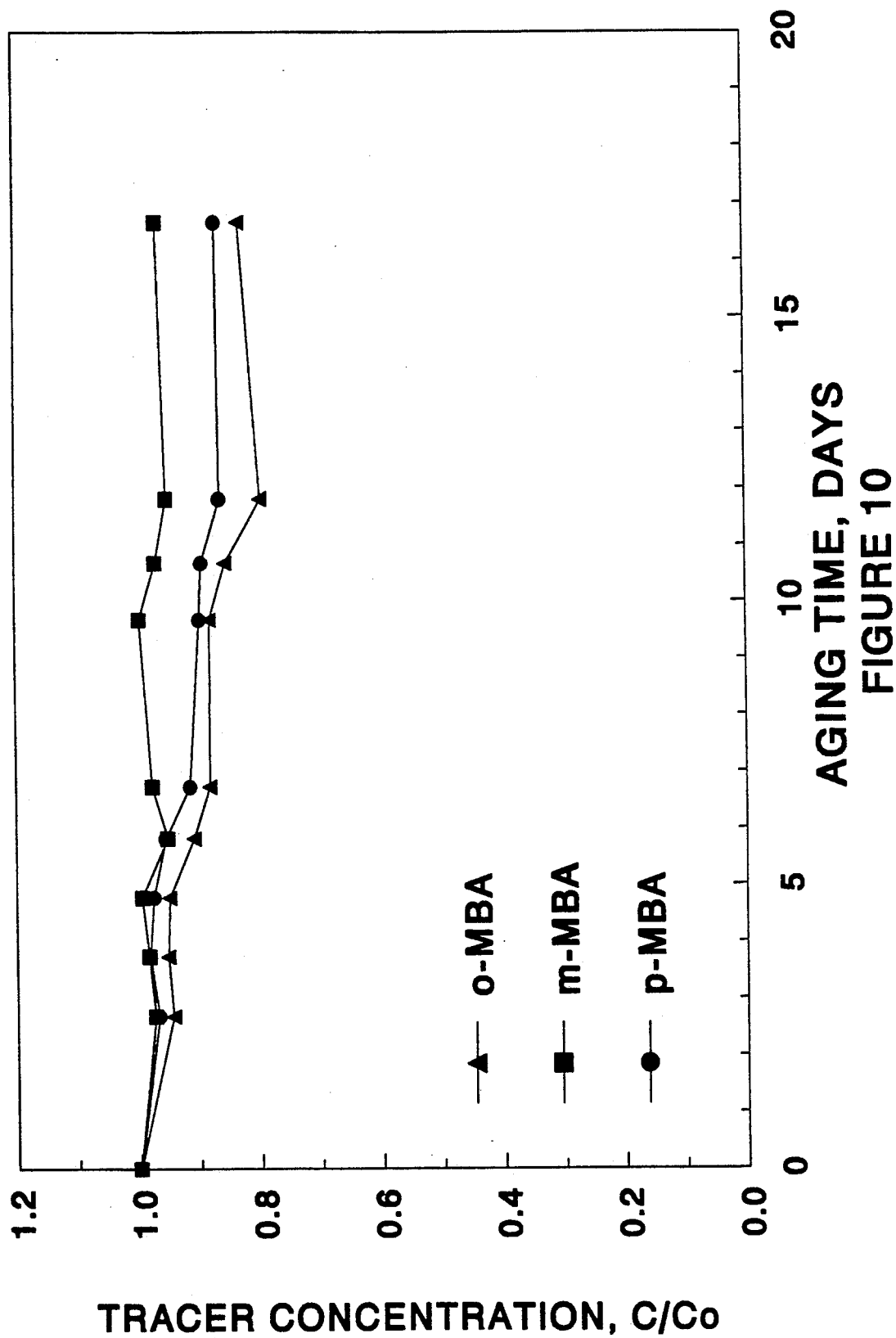
Figure 11:
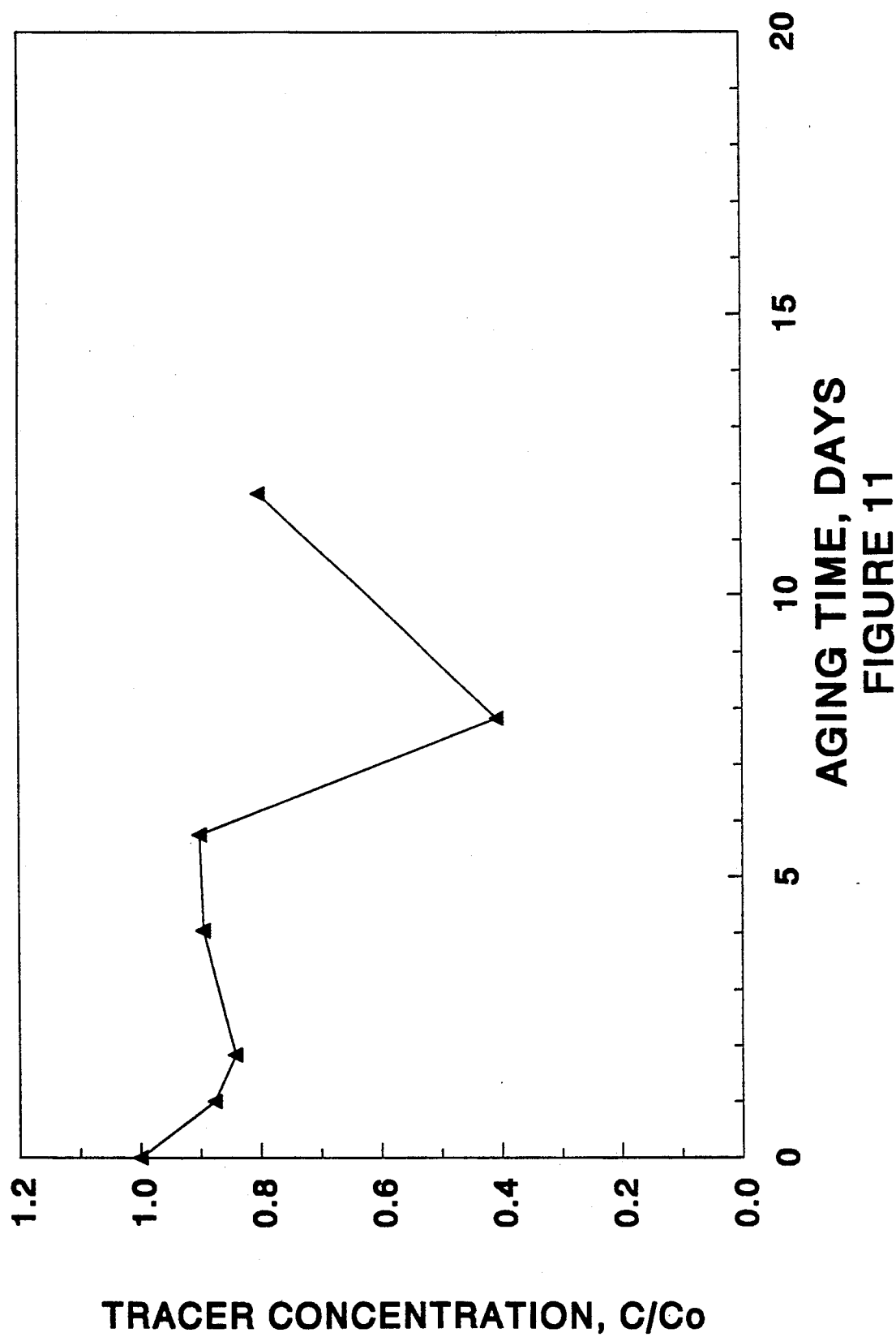
Figure 12:
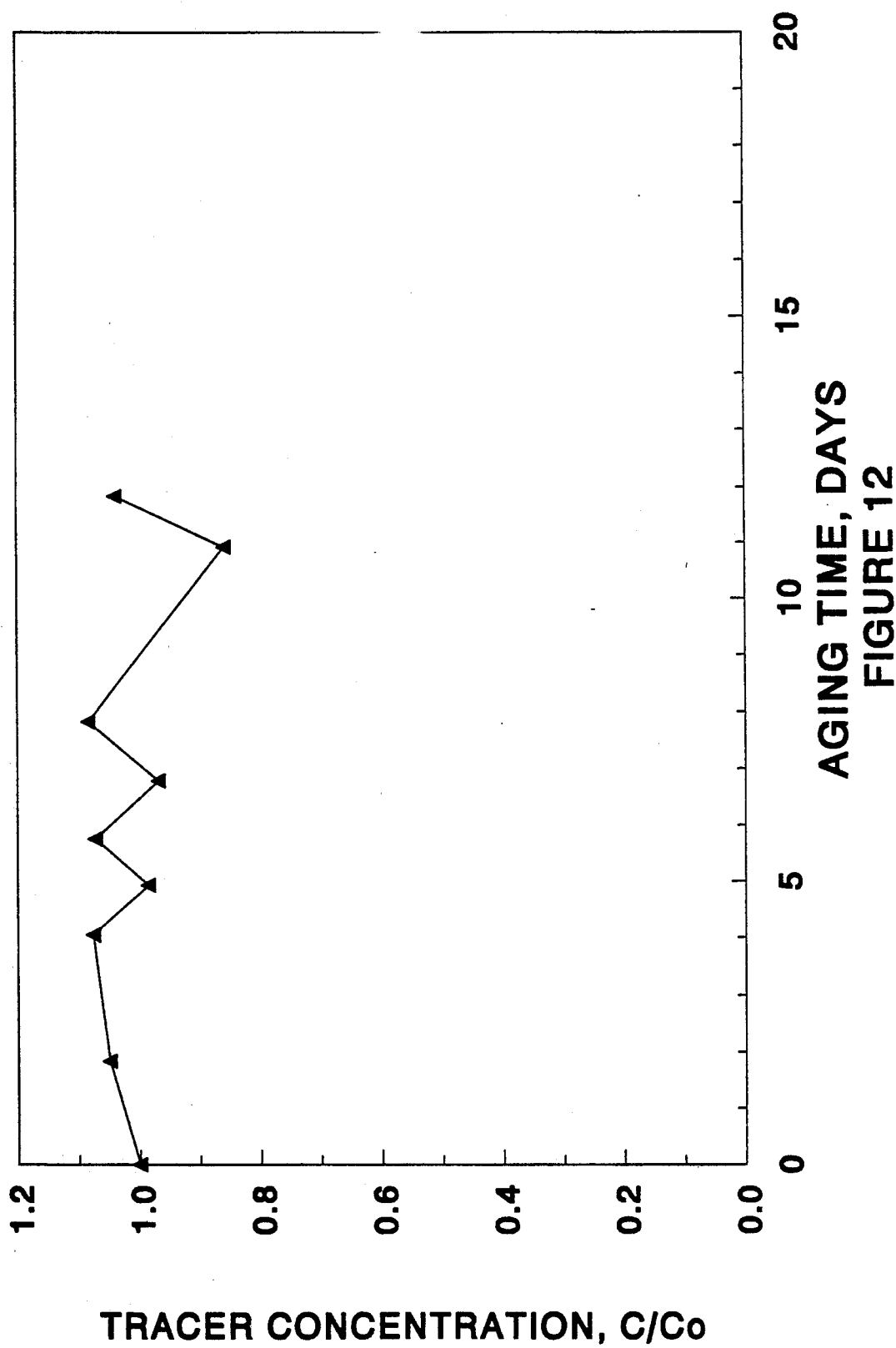
Figure 13:
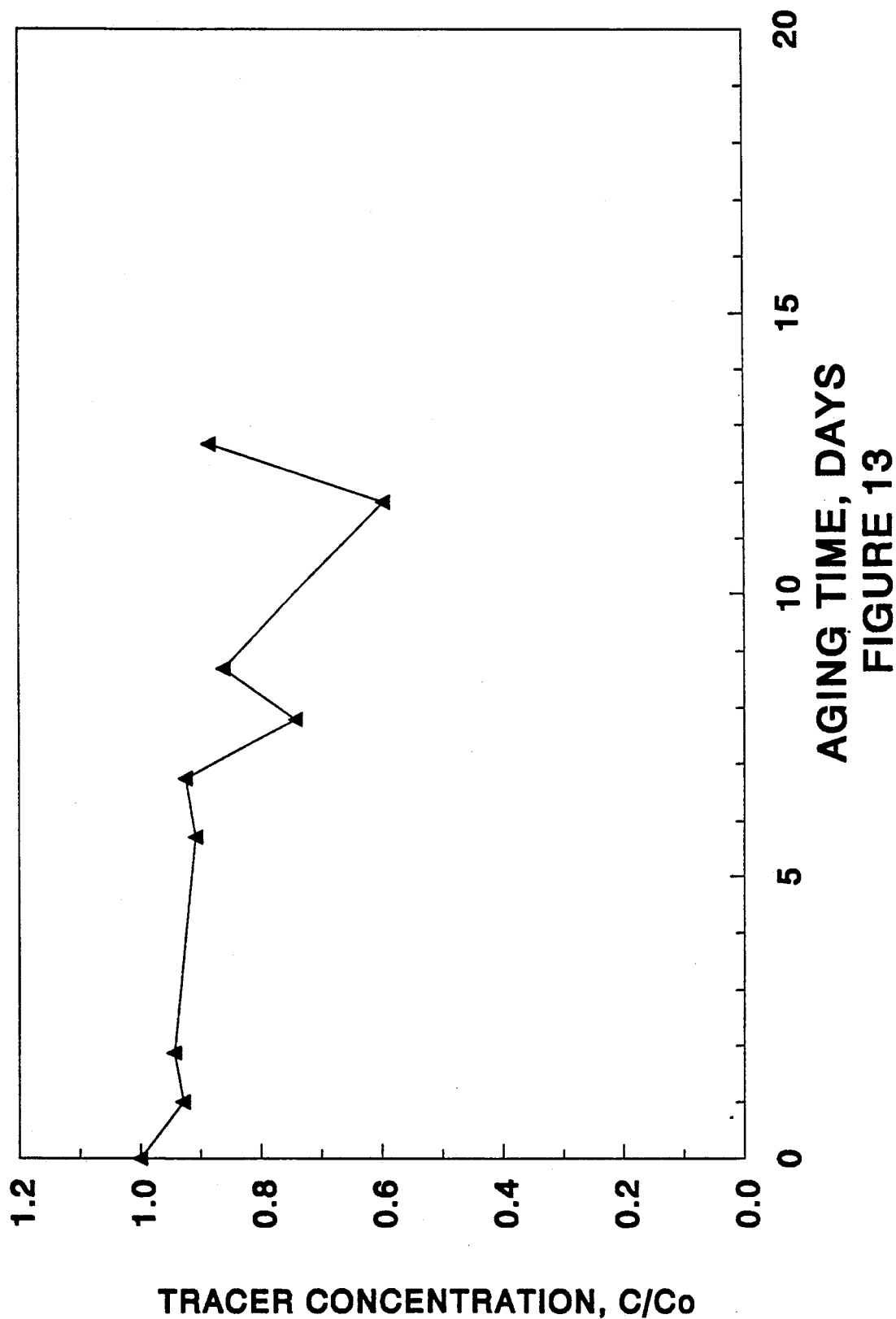

FIG. 5 is a graph depicting the results of stability tests of 1,5- and 2,6-naphthalenedisulfonic acids at about 260° C. (about 500° F.);

FIG. 6 is a graph depicting the results of stability tests of 1- and 2-naphthalenesulfonic acids (1-NSA and 2-NSA, respectively) at about 260° C. (about 500° F.);

FIG. 7 is a graph depicting the results of a stability test of 1,3,6-naphthalenetrisulfonic acid at about 260° C. (about 500° F.);

FIG. 8 is a graph depicting the results of stability tests of 1,5-, 1,6-, 2,3-, 2,6-, and 2,7-naphthalenediols at about 260° C. (about 500° F.);

FIG. 9 is a graph depicting the results of stability tests of pyridine and 2-methyl-5-ethylpyridine when aged at about 260° C. (about 500° F.) in the presence of a subterranean core material;

FIG. 10 is a graph depicting the results of stability tests of ortho-, meta-, and para-methylbenzoic acids when aged at about 260° C. (about 500° F.) in the presence of a subterranean core material;

FIG. 11 is a graph depicting the results of a stability test of aniline when aged at about 260° C. (about 500° F.) in the presence of a subterranean core material;

FIG. 12 is a graph depicting the results of a stability test of 1,2,4,5-benzene tetracarboxylic acid when aged at about 260° C. (about 500° F.) in the presence of a subterranean core material;

FIG. 13 is a graph depicting the results of stability tests of 1,5- and 2,6-naphthalenedisulfonic acids when aged at about 260° C. (about 500° F.) in the presence of a subterranean core material;

FIG. 14 is a graph depicting the results of stability tests of 1- and 2-naphthalenesulfonic acids (1-NSA and 2-NSA, respectively) when aged at about 260° C. (about 500° F.) in the presence of a subterranean core material; and FIG. 15 is a graph depicting the results of a stability test of 1,3,6-naphthalenetrisulfonic acid when aged at about 260° C. (about 500° F.) in the presence of a subterranean core material.

DETAILED DESCRIPTION OF THE INVENTION

In the present invention, at least one of the organic chemicals set forth in the following Table I is used as a tracer for monitoring the movement of one or more subterranean fluids.

TABLE I

Genus
benzene tetracarboxylic acid and salts thereof
Exemplary species:  1,2,4,5-benzene tetracarboxylic acid
sodium 1,2,4,5-benzene tetracarboxylate
methylbenzoic acid and salts thereof
Exemplary species:  ortho-methylbenzoic acid
meta-methylbenzoic acid
para-methylbenzoic acid
ammonium ortho-methybenzoate
potassium meta-methylbenzoate
lithium para-methylbenzoate
aniline
substituted aniline
Exemplary species:  halogenated aniline
dihalogenated aniline
N-alkyl aniline
N,N-dialkyl aniline
alkyl aniline
dialkyl aniline
alkoxy aniline
phenoxy aniline
pyridine
subsituted pyridine
Exemplary species:  alkylpyridine
dialkylpyridine
trialkylpyridine
aminoalkylpyridine
alkylaminopyridine
dialkylaminopyridine
aminopyridine

TABLE I-continued
diaminopyridine
acetylpyridine
phenylpyridine
hydroxypyridine
dihydroxypyridine
naphthalenesulfonic acid and salts thereof
Exemplary species:  1-naphthalenesulfonic acid
2-naphthalenesulfonic acid
calcium 1-naphthalenesulfonate
sodium 2-naphthalenesulfonate
naphthalenedisulfonic acid and salts thereof
Exemplary species:  1,5-naphthalenedisulfonic acid
2,6-naphthalenedisulfonic acid
potassium 1,5-naphthalenedisulfonate
ammonium 2,6-naphthalenedisulfonate
naphthalenetrisulfonic acid and salts thereof
Exemplary species:  1,3,6-naphthalenetrisulfonic acid
lithium 1,3,6-naphthalenetrisulfonate
naphthalenediol
Exemplary species:  1,4-naphthalenediol
1,5-naphthalenediol
1,6-naphthalenediol
2,3-naphthalenediol
2,6-naphthalenediol
2,7-naphthalenediol
alkyl benzene sulfonic acid and salts thereof
Exemplary species:  decyl benzene sulfonic acid
lauryl benzene sulfonic acid
ammonium decyl benzene sulfonate
sodium lauryl benzene sulfonate
alkyl toluene sulfonic acid and salts thereof
Exemplary species:  decyl toluene sulfonic acid
lauryl toluene sulfonic acid
lithium decyl benzene sulfonate
sodium lauryl toluene sulfonate
alkyl xylene sulfonic acid and salts thereof
Exemplary species:  decyl xylene sulfonic acid
lauryl xylene sulfonic acid
sodium decyl xylene sulfonate
ammonium lauryl xylene sulfonate
alpha-olefin sulfonic acid and salts thereof
Exemplary species:  hexadecyl alpha-olefin sulfonic acid
eicosyl alpha-olefin sulfonic acid
sodium hexadecyl alpha-olefin sulfonate
potassium eicosyl alpha-olefin sulfonate The salt moiety of the acids set forth in above Table I is generally selected from the group consisting of ammonium, alkali metals, and alkaline-earth metals. Preferably, the salt moiety is ammonium or an alkali metal. Of the alkali metals, sodium and potassium are especially preferred. Calcium is the preferred alkaline-earth metal.

The preferred carbon content of the alkyl and alkoxy substituents of the various tracers listed in Table I, supra, depends on the specific tracer and whether the tracer is being injected into an aqueous- or organic-based fluid. Accordingly, preferred (Pref.) carbon atom content ranges for each alkyl or alkoxy group present in these various tracers are enumerated in the following Table II.

TABLE II

| | Carbon Atom Content of Alkyl And Alkoxy Groups | | | | | |
|---|---|---|---|---|---|---|
| | Water-Based Fluid | | | Organic Based Fluid | | |
| Compound | Pref. | More Pref. | Most Pref. | Pref. | More Pref. | Most Pref. |
| N-alkyl aniline | 1-6 | 1-4 | 1-3 | 1-12 | 1-10 | 1-6 |
| N,N-dialkyl aniline | 1-9 | 1-5 | 1-3 | 1-12 | 1-10 | 1-6 |
| alkyl aniline | 1-4 | 1-3 | 1-2 | 1-12 | 1-10 | 1-6 |
| dialkyl aniline | 1-4 | 1-3 | 1-2 | 1-12 | 1-10 | 1-6 |
| alkoxy aniline | 1-4 | 1-3 | 1-2 | 1-12 | 1-10 | 1-6 |
| alkoxy pyridine | 1-4 | 1-3 | 1-2 | 1-12 | 1-10 | 1-6 |
| alkyl pyridine | 1-8 | 1-5 | 1-3 | 1-12 | 1-10 | 1-6 |
| dialkyl pyridine | 1-4 | 1-3 | 1-2 | 1-6 | 1-5 | 1-4 |
| trialkyl pyridine | 1-3 | 1-2 | 1 | 1-4 | 1-3 | 1-2 |
| aminoalkylpyridine | 1-8 | 1-6 | 1-4 | 1-10 | 1-8 | 1-6 |
| alkylaminopyridine | 1-8 | 1-6 | 1-4 | 1-10 | 1-8 | 1-6 |

TABLE II-continued

| Compound | Carbon Atom Content of Alkyl And Alkoxy Groups | | | | | |
|---|---|---|---|---|---|---|
| | Water-Based Fluid | | | Organic Based Fluid | | |
| | Pref. | More Pref. | Most Pref. | Pref. | More Pref. | Most Pref. |
| dialkylaminopyridine | 1-4 | 1-3 | 1-2 | 1-6 | 1-5 | 1-3 |
| alkyl benzene sulfonic acid and their salts | 1-30 | 8-20 | 10-18 | 1-36 | 12-30 | 16-24 |
| alkyl toluene sulfonic acid and their salts | 1-30 | 8-20 | 10-18 | 1-36 | 12-30 | 16-24 |
| alkyl xylene sulfonic acid and their salts | 1-30 | 8-20 | 10-18 | 1-36 | 12-30 | 16-24 |
| alpha-olefin sulfonic acid and their salts | 3-30 | 6-24 | 10-20 | 3-36 | 10-36 | 12-30 |

The tracers set forth in Table I, supra, are desirable because they are (a) stable at elevated temperatures (i.e., generally at least about 250° C. (about 482° F.), preferably at least about 260° C. (about 500° F.), more preferably at least about 275° C. (about 527° F.), and most preferably at least about 300° C. (about 572° F.)), (b) capable of being detected at low concentrations (e.g., generally at about 100 parts per billion (ppb), preferably at about 75 ppb, more preferably at about 50 ppb, yet more preferably at about 25 ppb, and even as low as 20, 15, 10, and 5 ppb), and/or (c) not adversely affected by the make-up of at least one subterranean formation (i.e., the tracers do not appreciably adsorb or react in the presence of the constituent minerals of the subterranean reservoir). In addition, a plurality of these tracers are capable of being measured by a single analytical technique.

Subterranean fluids whose movements are capable of being monitored by these tracers include, but are not limited to, geothermal brine, crude oil, ground water, hazardous waste, and injected fluids used in enhanced oil recovery operations, e.g., steam floods, carbon dioxide floods, caustic floods, micellar-polymer floods, and straight polymer floods. It is preferred that the tracer be non-foaming in order to avoid diverting the flow path of the injected fluid.

The total dissolved solids content of the injected fluids varies. For example, the total dissolved solids content of water employed in steam floods (prior to the addition of any additives such as surfactants) is generally less than about 100 ppm. Brines injected into a subterranean formation during oil production operations tend to have total dissolved solids contents typically from about 100 to about 100,000 ppm and more commonly about 500 to about 75,000. Exemplary total dissolved solids contents of some geothermal brines (which usually are at temperatures varying from about 204.4° to about 371.1° C. (about 400° to about 700° F.)) are listed below in Table III.

TABLE III

| Brine Source | Total Dissolved Solids, ppm |
|---|---|
| The Geysers, California | approximately 0 to 20 |
| Tiwi, Philippines | approximately 5,000 |
| Bulalo, Philippines | approximately 10,000 |
| Salton Sea, California | approximately 200,000 to 300,000 |

Water-soluble tracers are preferably employed when the tracer is added to an aqueous-based fluid being injected into a subterranean formation and organic-soluble tracers are preferably employed in those instances where the tracer is incorporated into an organic-based fluid injected into a subterranean formation. In use, the tracer is dissolved in a suitable solvent (i.e., water in the case of water-soluble tracers and an organic solvent or oil in the case of organic-soluble tracers) to make a concentrated solution. The concentrated solution generally contains at least about 10,000 parts per million (ppm) tracer. Some tracers are employed neat, i.e., without any prior dilution. The concentrated tracer-containing solution or neat tracer is typically either pulsed or gradually fed into the fluid injected into a formation (e.g., using a metering pump) before the wellhead of the injector well. A sufficient amount of the tracer concentrate or neat tracer is fed into the injection fluid so that the average concentration of the tracer in the injection fluid is generally about 500 to about 50,000 ppm, preferably about 2,500 to about 25,000 ppm, and more preferably about 5,000 to about 10,000 ppm. The average tracer concentration in the injected fluid is calculated using the following equation:

$$C_f = (C_{tc})(q_c)/(q_f + q_c)$$

where $C_f$ is the average concentration of the tracer in the final injected fluid, $C_{tc}$ is the tracer concentration in the tracer concentrate or neat tracer, $q_c$ is the flow rate of the tracer concentrate or neat tracer, and $q_f$ is the flow rate of the injected fluid prior to the incorporation of the tracer concentrate or neat tracer.

A geothermal field will be used to illustrate one process of the present invention. A geothermal field usually comprises one or more production wells for producing geothermal brine from one or more subterranean geothermal reservoirs. Heat is extracted from the produced brine and the resulting modified brine is either injected into a subterranean formation through one or more injection wells or disposed of in another manner. Occasionally, water or a different brine is injected to recharge the formation.

In order to determine whether the fluid injected into a specific injection well is adversely affecting the produced geothermal brines (e.g., causing a cooling effect), at least one of the tracers listed in the above Table I is incorporated into that injected fluid and at least one brine sample from each of one or more of the production wells (and preferably from each of all of the production wells) is periodically assayed for its presence.

To determine which of a plurality of injection wells is injecting fluids adversely impacting brine produced from one or more production wells, a different tracer is incorporated into each of a plurality of fluid streams injected into respective injection wells. In this version, samples of the brines produced from one or more of the production wells (preferably from each of the production wells) are also periodically analyzed for the presence of these tracers. By judiciously selecting the tracers, a single analysis is used to check each sample for the presence of all tracers employed in the monitoring program—thereby saving a significant amount of analytical time, effort, and money.

Another exemplary process of the present invention entails monitoring the fluids injected during a steam flood. In this version of the invention, the steam is typically injected using a 5-spot or 9-spot injection-producer pattern. Occasionally, early steam breakthrough occurs at a producer well. To determine which of the injection wells is channeling its injected fluid to the producer well, a different tracer is added to each of the steam injection wells designed to service the affected producer well. By analyzing samples of the produced fluids, the injection well responsible for the early breakthrough is identifiable and, once identified, remedial action can be taken.

In an additional version of the invention, the source of a hazardous waste is identified. For example, a hazardous waste can appear, among other places, in a subterranean potable water source or in the basement of a building. There may be two or more operators proximate the contaminated area handling the same hazardous waste. To determine which operator is responsible for the pollution (as well as the source of the pollution), a different tracer is incorporated into each of the operators' wastes. If a particular operator is handling the hazardous waste at more than one location, it is preferable to incorporate a different tracer into each waste that is processed at a separate location. By periodically analyzing samples from the polluted area, the operator and location responsible for the pollution can be identified and corrective action can then be commenced.

EXAMPLES

The following examples are intended to illustrate and not limit the invention—the invention being defined by the claims. A high performance liquid chromatography (HPLC) analytical procedure for simultaneously analyzing a single sample of a subterranean fluid for at least about 13 aromatic tracers is provided in Example 1. In Example 2, an HPLC analytical procedure is detailed for simultaneously analyzing a single sample of a subterranean fluid for at least about three basic tracers. An HPLC method for analyzing a subterranean fluid for about three or more acidic tracers is presented in Example 3. Stability tests were performed on various tracers in Example 4.

EXAMPLE 1

HPLC Procedure for Simultaneously Analyzing 13 Aromatic Tracers

A. Introduction

The following HPLC procedure is capable of measuring the concentration of 13 tracers in about 30 minutes. Detection limits range from about 5 to about 60 ppb. The only sample preparation required is dilution and filtration.

B. Protocol

1. Prepare the eluent by dissolving about 13.4 g $Na_2HPO_4.7H_2O$, about 6.9 g $NaH_2PO_4.H_2O$, and about 6.0 g tetrabutylammonium hydrogen sulfate in about 2 l of HPLC grade water. Water prepared by a Milli-Q purification system is adequate. Measure about 600 ml of the above buffer solution and about 400 ml of HPLC grade methanol in separate 1 l graduated cylinders. Add the buffer to the graduated cylinder containing the methanol. The buffer is made more reproducibly by measuring the components separately because of a volume contraction when the components are mixed. Because the methanol-buffer mixture effervesces, vent the mixture frequently while mixing. Filter the mixture through $0.5\mu$ fluoropore filter (Millipore Corp.) and degas it by sparging with helium.

2. Prepare a standard concentrate by accurately weighing into a 250 ml volumetric flask about 25 mg of each of 2,4-dimethylbenzene sulfonic acid, 2,5-dimethylbenzene sulfonic acid, 1-naphthalene sulfonic acid, 2-naphthalene sulfonic acid; about 50 mg of benzoic acid; and about 100 mg of each of 2,6-naphthalenedisulfonic acid, 1,5-naphthalenedisulfonic, o-methylbenzoic acid, m-fluorobenzoic acid, p-methylbenzoic acid, m-methylbenzoic acid, 2,3-dimethylbenzoic acid, and 3,4-dimethylbenzoic acid. Add about 100 ml of methanol and warm the solution to dissolve the standards. Bring to the mark with HPLC grade water. Dilute the standard concentrate about 3/50 with eluent to make a working standard.

3. Prepare samples by diluting them with eluent to obtain a final concentration below about 25 ppm.

4. Filter the samples and working standard through a $0.2\mu$ filter, and inject them into the chromatograph using the following conditions:

Injection volume: 25 $\mu l$.
Flow rate: 1.0 ml/ min.
Column: Apex C18, 4.6 mm $\times$ 250 mm, Jones Scientific, P.O. Box 280329, Lakewood, Colo. 80228-0329
Detector: UV at 224 nm, 0.02 Absorbance Units Full Scale (AUFS).

5. a. Calculate the slope of the calibration curve for each component.

$$Si = (Wi/250)(3/50)(1000/Ai)$$

where
Si = The slope of the calibration curve for component i in mg/l per area unit.
Wi = Weight of component used to make standard in mg.
1000 = Conversion from mg/ml to mg/l.
Ai = The integrated area of the peak for component i in the standard mixture.
250 = Volume of initial standard solution.
3/50 = Dilution correction.

b. Calculate the concentration of each component as follows:

$$Ci = (Si)(Bi)(Df)$$

where:
Ci = The concentration of component i in mg/l.
Si = The slope of the calibration curve for component i.
Bi = The integrated area of the peak for the component i in the sample.
Df = Dilution factor for the sample. For example, if the sample was diluted 1/10, Df = 10.

C. Discussion

The above described analytical technique is isocratic ion pair reversed phase high performance liquid chromatography with UV detection. The eluent contains a phosphate buffer to keep the carboxylic acids in their ionic form, tetrabutylammonium hydrogen sulfate as an ion pairing agent, and methanol to control retention. The detection wavelength is about 224 nm which represents a compromise between the optimum detection wavelengths of the individual components.

All of the tracers gave linear calibration curves with correlation coefficient $r^2 >= 0.999$. The calibration curves all pass very close to the origin, thus a single point calibration will suffice for most applications. The detection limits estimated for a signal to noise ratio of three are given below in Table IV. Detections limits will differ on other instruments. Lower detection limits are possible by using the optimum wavelength for a particular compound or group of compounds. However, changing the wavelength may increase the detection limit for other compounds. Alternatively, lower concentrations are detectable by using any number of preconcentration procedures know to those skilled in the art. The reproducibility of the method at about the 1–5 ppm level varied from about 0.21% to about 2.0% relative standard deviation (RSD). The overall average RSD was about 0.86%

TABLE IV

Multiple Tracer Analysis Detection Limits

| Retention Time (min) | Compound | Detection Limit (ppb) |
| --- | --- | --- |
| 5.43 | 2,6-Naphthalenedisulfonic acid | 5 |
| 6.11 | 1,5-Naphthalenedisulfonic acid | 6 |
| 7.21 | Benzoic acid | 13 |
| 8.96 | o-Methylbenzoic acid | 30 |
| 9.98 | m-Fluorobenzoic acid | 17 |
| 12.22 | p-Methylbenzoic acid | 18 |
| 12.88 | m-Methylbenzoic acid | 24 |
| 13.70 | 2,3-Dimethylbenzoic acid | 43 |
| 19.64 | 2,4-Dimethylbenzene sulfonic acid | 36 |
| 20.75 | 2,5-Dimethylbenzene sulfonic acid | 50 |
| 21.77 | 3,4-Dimethylbenzoic acid | 60 |
| 25.70 | 1-Naphthalene sulfonic acid | 12 |
| 28.26 | 2-Naphthalene sulfonic acid | 5 |

EXAMPLE 2

A. Introduction

This procedure pertains to the analysis of three basic aromatic tracers. Detection limits are under about 500 ppb for these tracers. The only sample preparation required is dilution and filtration.

B. Protocol

1. Prepare the eluent by mixing about 760 ml HPLC grade water, about 240 ml acetonitrile, and about 1 ml of triethylamine. Water prepared by a Milli-Q purification system is adequate. Filter the mixture through 0.5μ fluoropore filter (Millipore Corp.) and degas it by sparging with helium. (Fluoropore filters are not wetted by aqueous solutions. Before filtering the eluent, wet the filter with a few drops of methanol.)

2. Prepare a standard concentrate by accurately weighing about 100 mg each of pyridine, aniline, and 2-methyl-5-ethylpyridine into a 100 ml volumetric flask. Bring to the mark with water and shake to dissolve. Dilute the standard concentrate about 10/100 and about 1/100 with water to make working standards.

3. Prepare samples by diluting them with eluent to obtain a final concentration below about 100 ppm.

4. Filter the samples and working standard through a 0.2μ filter, and inject them into the chromatograph using the following conditions:

Injection volume: 25 μl.
Flow rate: 1.5 ml/ min.
Column: Apex C18, 4.6 mm×250 mm, Jones Scientific, P.O. Box 280329, Lakewood, Colo. 80228-0329
Saturator Column: Because of the high pH of the eluent, a silica saturator column should be installed between the pump and injector.
Detector: UV at 253 nm, 0.05 AUFS.

5. a. Calculate the slope of the calibration curve for each component.

$$Si = (Wi/100)(Dc)(1000/Ai)$$

where:
Si = The slope of the calibration curve for component i in mg/l per area unit.
Wi = Weight of component used to make standard in mg.
1000 = Conversion from mg/ml to mg/l.
Ai = The integrated area of the peak for component i in the standard mixture.
100 = Volume of initial standard solution.
Dc = Dilution correction e.g., Dc = 0.01 for a 1 to 100 dilution.

b. Calculate the concentration of each component as follows:

$$Ci = (Si)(Bi)(Df)$$

where
Ci = The concentration of component i in mg/l.
Si = The slope of the calibration curve for component i.
Bi = The integrated area of the peak for component i in the sample.
Df = Dilution factor for the sample. For example, if the sample was diluted 1/10, Df = 10.

C. Discussion

The analytical technique is isocratic reversed phase high performance liquid chromatography with UV detection. The eluent contains triethylamine to reduce peak tailing and acetonitrile to control retention. The detection wavelength is about 253 nm which represents a compromise between the optimum detection wavelengths of the individual components.

All of the compounds gave linear calibration curves. The correlation coefficient ($r^2$) was greater then about 0.999 for the pyridines and greater than about 0.9999 for the other compounds. The calibration curves all pass very close to the origin, thus a single point calibration will suffice for most applications. For the greatest accuracy, the concentration of the calibration standard should be within a factor of about 10 of sample concentration. The detection limits estimated for a signal to noise ration of three are given in Table V, infra. Detections limits will differ on other instruments. Lower detection limits are possible by using the optimum wavelength for a particular compound or group of compounds. However, changing the wavelength may increase the detection limit for other compounds. The reproducibility of the methods varied from about 0.25% to about 1.3% RSD. The overall average RSD was about 0.43%

TABLE V

Multiple Basic Tracer Analysis Detection Limits

| Retention Time (min) | Compound | Detection Limit (ppb) |
| --- | --- | --- |
| 3.38 | Pyridine | 200 |
| 5.91 | Aniline | 350 |
| 14.15 | 2-Methyl-5-ethylpyridine | 500 |

EXAMPLE 3

A. Introduction

An HPLC analysis of tracers measures three benzene polycarboxylic acids. Detection limits are under about 20 ppb for these acids. The only sample preparation required is dilution and filtration.

B. Protocol

1. Prepare the eluent by dissolving about 13.4 g $Na_2HPO_4.7H_2O$, about 6.9 g $NaH_2PO_4.H_2O$, and about 6.0 g tetrabutylammonium hydrogen sulfate in about 2 l of HPLC grade water. Water prepared by a Milli-Q purification system is adequate. Measure about 725 ml of the above buffer solution and about 275 ml of HPLC grade methanol in separate 1 l graduated cylinders. Add the buffer to the graduate containing the methanol. The buffer is made more reproducibly by measuring the components separately because of a volume contraction when the components are mixed. Because the methanol-buffer mixture effervesces, vent the mixture frequently while mixing. Filter the mixture through $0.5\mu$ fluoropore filter (Millipore Corp.) and degas it by sparging with helium. (Fluoropore filters are not wetted by aqueous solutions. Before filtering the eluent, wet the filter with a few drops of methanol.)

2. Prepare a standard concentrate by accurately weighing the amounts listed into a 250 ml volumetric flask.

| | |
|---|---|
| Terephthalic acid | 100 mg |
| Isophthalic acid | 50 mg |
| 1,2,4,5-Benzenetetracarboxylic acid | 60 mg |

Add about 200 mg of sodium hydroxide (2 pellets) and bring to the mark with water. Shake the flask until all of the material is dissolved. Dilute the standard concentrate about 10/100 and about 1/100 with water to make working standards.

3. Prepare samples by diluting them with eluent to obtain a final concentration below about 50 ppm.

4. Filter the samples and working standard through a $0.2\mu$ filter, and inject them into the chromatograph using the following conditions:
Injection volume: 25 $\mu$l.
Flow rate: 1.0 ml/ min.
Column: Apex C18, 4.6 mm×250 mm, Jones Scientific, P.O. Box 280329, Lakewood, Colo. 80228-0329
Detector: UV at 215 nm, 0.04 AUFS.

5 a. Calculate the slope of the calibration curve for each component.

$$Si = (Wi/250)(Dc)(1000/Ai)$$

where:

$Si$ = The slope of the calibration curve for component i in mg/l per area unit.
$Wi$ = Weight of component used to make standard in mg.
$1000$ = Conversion from mg/ml to mg/l.
$Ai$ = The integrated area of the peak for component i in the standard mixture.
$250$ = Volume of initial standard solution.
$Dc$ = Dilution correction e.g., $Dc = 0.01$ for a 1 to 100 dilution.

b. Calculate the concentration of each component as follows:

$$Ci = (Si)(Bi)(Df)$$

where:

$Ci$ = The concentration of component i in mg/l.
$Si$ = The slope of the calibration curve for component i.
$Bi$ = The integrated area of the peak for the component i in the sample.
$Df$ = Dilution factor for the sample. For example, if the sample was diluted 1/10, $Df = 10$.

C. Discussion

The analytical technique is isocratic ion pair reversed phase high performance liquid chromatography with UV detection. The eluent contains a phosphate buffer to keep the carboxylic acids in their ionic form, tetrabutylammonium hydrogen sulfate as an ion pairing agent, and methanol to control retention. The detection wavelength is about 215 nm which represents a compromise between the optimum detection wavelengths of the individual components.

All of the compounds gave linear calibration curves. The correlation coefficient ($r^2$) was greater than about 0.9999 for these compounds. The calibration curves all pass very close to the origin, thus a single point calibration will suffice for most applications. For the greatest accuracy, the concentration of the calibration standard should be within a factor of about 10 of sample concentration. The detection limits estimated for a signal to noise ration of three are given below in Table VI. Detections limits will differ on other instruments. Lower detection limits are possible by using the optimum wavelength for a particular compound or group of compounds. However, changing the wavelength may increase the detection limit for other compounds. The reproducibility of the methods varied from about 0.25% to about 1.3% RSD. The overall average RSD was about 0.43%

TABLE VI

| Multiple Acidic Tracer Analysis Detection Limits | | |
|---|---|---|
| Retention Time (min) | Compound | Detection Limit (ppb) |
| 6.08 | Terephthalic acid | 20 |
| 8.09 | Isophthalic acid | 15 |
| 9.30 | 1,2,4,5 Benzene tetracarboxylic acid | 15 |

EXAMPLE 4

The following procedure was employed for each tracer tested. A tracer was dissolved in synthetic Tiwi water at a nominal concentration of about 100 ppm. The resulting solution was purged with oxygen-free nitrogen for about 1 hour to reduce the oxygen content to about 20 ppb. Aliquots of the oxygen-reduced solution were transferred to ten glass capillary tubes under a nitrogen atmosphere. The sample-containing tubes were flame sealed under a small vacuum and placed in a stainless steel tube. Next, each stainless steel tube was partially filled with water and sealed. The sealed tubes were aged in an oven at about 260° C. (about 500° F.). Each working day, a tube was removed and cooled. After all the tubes were removed, they were analyzed using HPLC. Each compound which showed only slight degradation after about 10 to about 14 days was tested again with core material from the Tiwi reservoir (Matlibong #14) present. The results of these tests are plotted in FIGS. 1-15.

As shown in FIGS. 1-15, exemplary tracers of the present invention tested in Example 4 are thermally stable at a temperature of at least about 260° C. and are not adversely affected by the presence of a core material from the Tiwi geothermal reservoir.

Although the present invention has been described in considerable detail with reference to some preferred versions, other versions are possible. Therefore, the spirit and scope of the appended claims should not necessarily be limited to the description of the preferred versions contained herein.

What is claimed is:

1. A process for monitoring the flow of a subterranean fluid comprising the steps of:
   (a) injecting a tracer-containing fluid into at least one injection well; and
   (b) analyzing at least one sample from at least one producing source,
wherein the tracer comprises an organic compound selected from the group consisting of benzene tetracarboxylic acid, salts thereof, naphthalenediol, and mixtures thereof.

2. The process of claim 1 wherein the tracer is selected from the group consisting of benzene tetracarboxylic acid, salts thereof, and mixtures thereof.

3. The process of claim 1 wherein the tracer is selected from the group consisting of 1,2,4,5-benzene tetracarboxylic acid, 1,2,4,5-benzene tetracarboxylate, and mixtures thereof.

4. The process of claim 1 wherein the tracer comprises naphthalenediol.

5. The process of claim 1 wherein the tracer is selected from the group consisting of 1,4-naphthalenediol, 1,5-naphthalenediol, 1,6-naphthalenediol, 2,3-naphthalenediol, 2,6-naphthalenediol, 2,7-naphthalenediol, and mixtures thereof.

6. A process for monitoring the flow of x subterranean fluids, the process comprising the sequential steps of:
   (a) injecting x tracer-containing fluids into x respective injection wells, each of the x tracers being different with at least one of the tracers being an organic compound selected from the group consisting of benzene tetracarboxylic acid, salts of the foregoing acid, naphthalenediol, and mixtures thereof, and x being a positive integer of at least 2; and
   (b) analyzing at least one sample from at least one producing source for each of the x tracers.

7. The process of claim 6 wherein x is 2 and at least one producing source is a producer well.

8. The process of claim 6 wherein one tracer is selected from the group consisting of benzene tetracarboxylic acid, salts thereof, and mixtures thereof.

9. The process of claim 6 wherein one tracer comprises naphthalenediol.

10. A system for monitoring a subterranean fluid, the system comprising:
    (a) at least one means for sampling a subterranean fluid;
    (b) at least one injection well for injecting a tracer-containing fluid into at least a portion of a subterranean formation, the sampling means and injection well being in fluid communication; and
    (c) the tracer-containing fluid in at least a portion of the injection well, wherein the tracer is selected from the group consisting of benzene tetracarboxylic acid, salts thereof, naphthalenediol, and mixtures thereof.

11. A composition comprising:
    (a) a fluid selected from the group consisting of crude oil and brine; and
    (b) a compound selected from the group consisting of benzene tetracarboxylic acid, salts thereof, naphthalenediol, and mixtures thereof, wherein prior to combining the compound and the brine, the brine has a total dissolved solids content of at least about 500 ppm.

12. A process for monitoring the flow of x subterranean fluids, the process comprising the sequential steps of:
    (a) injecting x tracer-containing fluids into x respective injection wells, each of the x tracers being different with one tracer being aniline, wherein x is a positive integer of at least 2; and
    (b) analyzing at least one sample from at least one producing source for each of the x tracers.

13. A process for monitoring the flow of x subterranean fluids, the process comprising the sequential steps of:
    (a) injecting x tracer-containing fluids into x respective injection wells, each of the x tracers being different with at least one of the tracers being an organic compound selected from the group consisting of naphthalenesulfonic acid, naphthalenedisulfonic acid, naphthalenetrisulfonic acid, salts of the foregoing acids, and mixtures thereof, wherein x is a positive integer of at least 2; and
    (b) analyzing at least one sample from at least one producing source for each of the x tracers.

14. The process of claim 13 wherein one tracer is selected from the group consisting of naphthalenesulfonic acid, salts thereof, and mixtures thereof.

15. The process of claim 13 wherein one tracer is selected from the group consisting of naphthalenedisulfonic acid, salts thereof, and mixtures thereof.

16. The process of claim 13 wherein one tracer is selected from the group consisting of naphthalenetrisulfonic acid, salts thereof, and mixtures thereof.

17. A process for monitoring the flow of x subterranean fluids, the process comprising the sequential steps of:
    (a) injecting x tracer-containing fluids into x respective injection wells, each of the x tracers being different wherein one tracer is selected from the group consisting of alpha-olefin sulfonic acid, salts thereof, and mixtures thereof, wherein x is a positive integer of at least 2; and
    (b) analyzing at least one sample from at least one producing source for each of the x tracers.

18. A process for monitoring the flow of a subterranean fluid comprising the steps of:
    (a) injecting a tracer-containing fluid into at least one injection well; and
    (b) analyzing at least one sample from at least one producing source,
wherein the tracer comprises an organic compound selected from the group consisting of pyridine, 2-methyl-5-ethylpyridine, and mixtures thereof.

19. A composition comprising:
    (a) a fluid selected from the group consisting of crude oil and brine; and
    (b) a compound selected from the group consisting of alpha-olefin sulfonic acid and salts thereof, wherein the olefin moiety contains at least about 3 carbon atoms and prior to combining the compound and the brine, the brine has a total dissolved solids content of at least about 500 ppm.

* * * * *